(12) United States Patent
Hirochika et al.

(10) Patent No.: US 7,271,314 B1
(45) Date of Patent: Sep. 18, 2007

(54) METHOD FOR DISRUPTING GENES USING TOBACCO RETROTRANSPOSON

(75) Inventors: Hirohiko Hirochika, Ibaraki (JP); Hiroyuki Okamoto, Ibaraki (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 0 days.

(21) Appl. No.: 09/979,430

(22) PCT Filed: May 22, 1999

(86) PCT No.: PCT/JP99/02749

§ 371 (c)(1),
(2), (4) Date: Feb. 19, 2002

(87) PCT Pub. No.: WO00/71699

PCT Pub. Date: Nov. 30, 2000

(51) Int. Cl.
*C12N 15/09* (2006.01)
*C12N 15/82* (2006.01)
*A01H 5/00* (2006.01)

(52) U.S. Cl. .................. 800/278; 800/298; 800/306; 435/69.1; 435/468; 435/430

(58) Field of Classification Search .............. 800/298, 800/278, 306, 295; 435/468, 430, 69.1, 430.1
See application file for complete search history.

(56) References Cited

OTHER PUBLICATIONS

Casacuberta et al. EMBO J. 14:2670-2678 (1995).*
Hirochika et al The EMBO Journal, vol. 12 (6), pp. 2521-2528 (1993).*
Hirochika et al (PNAS (1996) 93:7783-7788.*
Feuerbach, F. et al., "Retrovirus-Like End Processing of the Tobacco Tnt1 Retrotransposon Linear Intermediates of Replication", *Journal of Virology* 71(5):4005-4015, 1997.
Results from a summarized group of a special research area, based on molecular variable plant organ plan "A Plan Concerning Plant Organs", Research Result Proceedings of 1995 (1995), p. 114-115 (English abstract translation).
Hirochika et al., *The Plant Cell*, 8:725-734 (1996).

* cited by examiner

*Primary Examiner*—Medina A. Ibrahim
(74) *Attorney, Agent, or Firm*—Perkins Coie LLP

(57) ABSTRACT

The present invention relates to a method for disrupting a gene in a plant using a tobacco retrotransposon, comprising the steps of introducing the retrotransposon into the plant, and culturing and regenerating the plant, into which the retrotransposon is introduced, to produce a transformed plant.

2 Claims, 3 Drawing Sheets

SEQUENCE LISTING

<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Description of artificial sequence:

-continued

Tto1-specific primer

<400> SEQUENCE: 1
tggatatgaa tagtgcccgt atgg                                          24

<210> SEQ ID NO 2
<211> LENGTH: 24
<212> TYPE: DNA
<213> ORGANISM: Artificial Sequence
<220> FEATURE:
<223> OTHER INFORMATION: Description of artificial sequence:
      Tto1-specific primer

<400> SEQUENCE: 2
tactctaacc aaagctctga tacc                                          24

<210> SEQ ID NO 3
<211> LENGTH: 16
<212> TYPE: DNA
<213> ORGANISM: Artificial Sequence
<220> FEATURE:
<223> OTHER INFORMATION: Description of artificial sequence: arbitrary
      primer for amplification of genomic sequence flanking Tto1
<220> FEATURE:
<221> NAME/KEY: misc_feature
<222> LOCATION: 1, 11
<223> OTHER INFORMATION: n = a,t,c, or g

<400> SEQUENCE: 3
ngtcgaswga nawgaa                                                   16

<210> SEQ ID NO 4
<211> LENGTH: 16
<212> TYPE: DNA
<213> ORGANISM: Artificial Sequence
<220> FEATURE:
<223> OTHER INFORMATION: Description of artificial sequence: arbitrary
      primer for amplification of genomic sequence flanking Tto1
<220> FEATURE:
<221> NAME/KEY: misc_feature
<222> LOCATION: 3, 11
<223> OTHER INFORMATION: n = a,t,c, or g

<400> SEQUENCE: 4
gtncgaswca nawgtt                                                   16

<210> SEQ ID NO 5
<211> LENGTH: 16
<212> TYPE: DNA
<213> ORGANISM: Artificial Sequence
<220> FEATURE:
<223> OTHER INFORMATION: Description of artificial sequence: arbitrary
      primer for amplification of genomic sequence flanking Tto1
<220> FEATURE:
<221> NAME/KEY: misc_feature
<222> LOCATION: 5, 10, 13
<223> OTHER INFORMATION: n = a,t,c, or g

<400> SEQUENCE: 5
wgtgnagwan canaga                                                   16

<210> SEQ ID NO 6
<211> LENGTH: 21
<212> TYPE: DNA
<213> ORGANISM: Artificial Sequence
<220> FEATURE:
<223> OTHER INFORMATION: Description of artificial sequence: sequencing
      primer

```
<400> SEQUENCE: 6
ctcactaagg agagttgcat c                                              21
```

METHOD FOR DISRUPTING GENES USING TOBACCO RETROTRANSPOSON

This application claims priority to application no. PCT/JP99/02749 filed 22 May 1999, now publication no. WO 00/71699 published 30 Nov. 2000 which is incorporated herein by reference.

TECHNICAL FIELD

The present invention relates to gene disruption and gene isolation by transposon tagging. More particularly, the present invention relates to gene disruption in a heterologous plant (e.g., *Arabidopsis*) using a tobacco retrotransposon.

BACKGROUND ART

Gene disruption by transposable elements is an important means for isolating useful genes and analyzing their functions. *Arabidopsis* has been studied as a model plant, in which T-DNA and transposons are used as insertion elements.

In the case of T-DNA, when a Ti plasmid is introduced into a plant using *Agrobacterium*, the T-DNA, which is carried on the Ti plasmid, is inserted into one of the plant chromosomes, thereby disrupting a gene. However, it has been reported that in gene disruption experiments using T-DNA, T-DNA is not successfully integrated in 50 to 60% of mutants, so that the T-DNA does not substantially function as a tag.

In the case of a transposon, gene disruption occurs during the process of transformation or in the subsequent process of transposition. Transposons are mutagenic genes which are ubiquitous in the genomes of animals, yeast, bacteria, and plants. Transposons are classified into two categories according to their mechanism of transposition. Class II transposons of class II undergo transposition in the form of DNA without replication. Class I transposons of class I are also called retrotransposons. Retrotransposons undergo replicative transposition through RNA as an intermediate.

Examples of class II transposons include the Ac/Ds, Spm/dSpm and Mu elements of maize (*Zea mays*) (Fedoroff, 1989, Cell 56, 181–191; Fedoroff et al., 1983, Cell 35, 235–242; Schiefelbein et al., 1985, Proc. Natl. Acad. Sci. USA 82, 4783–4787), and the Tam element of *Antirrhinum* (*Antirrhinum majus*) (Bonas et al., 1984, EMBO J, 3, 1015–1019). Class II transposons are widely used for gene isolation by transposon tagging. This technique utilizes a specific property of transposons. When a transposon transposes within a genome and integrates into a certain gene, the gene is physically or structurally modified, and so the phenotype controlled by the gene is changed. If a phenotypic change can be detected, the affected gene may be isolated (Bancroft et al., 1993, The Plant Cell, 5, 631–638; Colasanti et al., 1998, Cell, 93, 593–603; Gray et al., 1997, Cell, 89, 25–31; Keddie et al., 1998, The Plant Cell, 10, 877–887; Whitham et al., 1994, Cell, 78, 1101–1115). However, an untagged mutant has been reported, in which the transposon is excised during DNA transposon tagging (Bancroft et al., 1993, The Plant Cell, 5, 631–638). Transposons have a tendency to transpose in the vicinity of insertion sites within chromosomes (Bancroft and Dean, 1993, Genetics, 134, 1221–1229; Keller et al., 1993, Theor. Appl. Genet, 86, 585–588). A transposon which can transpose randomly into chromosomes is desired in order to produce disruption lines covering all possible genes. However, these transposons integrate into particular target sites. A gene disruption system using different from those described above is desired.

Class I transposons were originally identified and characterized in Drosophila and yeast. A recent study has revealed that retrotransposons are ubiquitous and dominant in plant genomes (Bennetzen, 1996, Trends Microbiol., 4, 347–353; Voytas, 1996, Science, 274, 737–738). It appears that most retrotransposons are an integratable but non-transposable unit. Retrotransposons have LTRs in the forward direction at each end, and regions encoding a gag protein constituting a virus-like particle and a reverse transcriptase pol protein between the two LTRs. RNA transcribed from a LTR promoter is reverse-transcribed by the pol protein into cDNA which is in turn inserted into a host chromosome. Transposition of a retrotransposon is performed by a protein encoded by the retrotransposon itself and there is no excision mechanism. Therefore, use of retrotransposons is an excellent gene disruption technique.

Recently, it has been reported that some retrotransposons are activated under stressful conditions, such as wounding, pathogen attack, and culture (Grandbastien, 1998, Trends in Plant Science, 3, 181–187; Wessler, 1996, Curr. Biol., 6, 959–961; Wessler et al., 1995, Curr. Opin. Genet. Devel., 5, 814–821). For example, activation of the tobacco retrotransposons Tnt1A and Tto1, and the rice retrotransposon Tos17 was found to occur under stressful conditions (Pouteau et al., 1994, Plant J., 5, 535–542; Takeda et al., 1988, Plant Mol. Biol., 36, 365–376; Hirochika et al., 1996, Proc. Natl. Acad. Sci. USA, 93, 7783–7788).

In rice, the rice retrotransposon Tos17 is activated by culture and can transpose into a gene (Hirochika et al., Proc. Natl. Acad. Sci. USA, 93, 7783–7788 (1996)). Therefore, Tos17 has been utilized as a means for mass gene disruption in rice.

In *Arabidopsis thaliana*, no retrotransposons having transposition activity have been isolated. It has been reported that the tobacco retrotransposon Tnt1, isolated by Grandbastien et al., is transposed in the process of introducing Tnt1 into *Arabidopsis* by transformation. However, it has yet to be clarified whether or not Tnt1 can be transposed into a gene (Lucas et al., 1995, EMBO J., 14, 2364–2393). It has been found that the tobacco retrotransposon Tto1 is transposed during the process of transformation into *Arabidopsis* (Hirochika and Kakutani, in preparation). Tto1 is also transposed in rice by culture (Hirochika et al., 1996, Plant, Cell, 8, 725–734), suggesting that Tto1 is transposable in a wide range of hosts. However, the frequency of transposition varies from line to line, and a high frequency of transposition is not necessarily reproducible.

DISCLOSURE OF THE INVENTION

The tobacco retrotransposon Tto1 was studied as to whether or not it can also transpose in *Arabidopsis*, causing gene disruption. *Arabidopsis* having a low copy number of Tto1 was cultured and regenerated. The transcription level of Tto1 and sequences flanking a Tto1 target site were systematically analyzed. As a result, Tto1 was transposed in a cultured cell, and the cloned cell was subsequently regenerated into a plant with a disrupted gene. The sequences flanking Tto1 were amplified and subjected to sequencing and homology analysis. As a result, it was recognized that Tto1 had been inserted into various genes.

The above-described result indicates that Tto1 provides a novel means for gene isolation by transposon tagging in *Arabidopsis*, which is not believed to have an active endogenous retrotransposon. The present invention is the first study that shows the possibility of gene disruption and gene isolation using a retrotransposon in *Arabidopsis*. The present invention has demonstrated that gene disruption and gene isolation by transposon tagging can also be performed using a retrotransposon which is heterologous but not endogenous.

The present invention relates to a method for disrupting a gene in a plant using a tobacco retrotransposon, comprising the steps of: introducing the retrotransposon into the plant; and culturing and regenerating the plant, into which the retrotransposon is introduced, to produce a plant with a disrupted gene.

In one embodiment of this invention, the retrotransposon is Tto1.

In one embodiment of this invention, the plant is a plant other than tobacco. Preferably, the plant is a crop plant. Preferably, the plant is *Arabidopsis*.

In one embodiment of this invention, the plant, into which the retrotransposon is introduced, has a small copy number of retrotransposons. The small copy number means 1 to 5 copies, preferably 1 to 3 copies, more preferably 1 to 2 copies, and most preferably one copy.

In one embodiment of this invention, the method further comprises the steps of: obtaining a descendant plant from the plant with a disrupted gene; and culturing and regenerating a tissue of the descendant plant into a plant body.

BEST MODE FOR CARRYING OUT THE INVENTION

Figure 1:
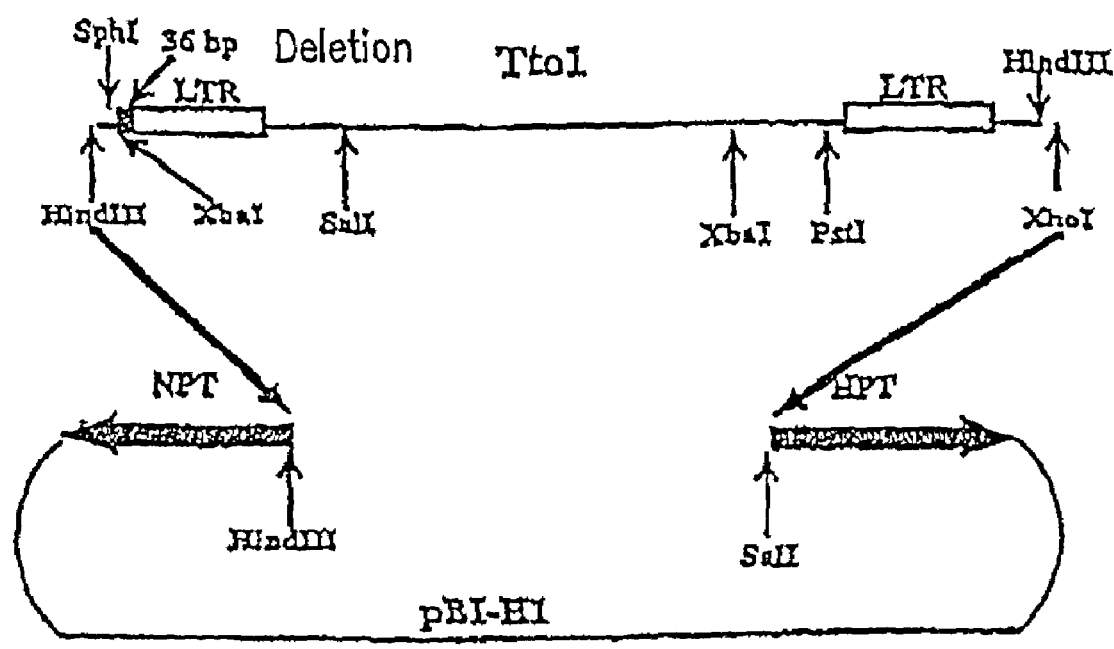
FIG. 1 is a diagram showing the structure of pBITto1 (−36).

According to the present invention, a method for disrupting a gene in a plant by introducing a tobacco retrotransposon is provided.

The term "disrupt a gene" as used herein refers to introducing DNA into cells, and screening for recombinant cells, obtained by transposition in order to introduce mutation into a specific target gene, thereby disrupting a gene. Therefore, in order to achieve gene disruption in the present invention, not only is a retrotransposon simply introduced into a plant cell, but also the retrotransposon has to be integrated into the genome of the plant cell. The term "transpose" as used herein refers to an event when an integrated retrotransposon is further integrated into another site in the genome.

A tobacco retrotransposon as used herein is preferably Tto1. Tto1 is a retrotransposon of Ty1/copia having an ORF of 1338 amino acids, a full length of 5.3 kb and a 574 bp LTR at each end. Tto1 is activated in tobacco by stress, such as culture, wounding, jasmonic acid, and viral infection. It is known that in tobacco, transposition of Tto1 is activated by culture. In the present invention, Tto1 was transposed in *Arabidopsis*, a plant heterologous to tobacco, leading to gene disruption in *Arabidopsis*.

The term "plant" as used herein refers to any plant into which a gene can be introduced. A "plant" includes monocotyledons and dicotyledons. Such a plant includes *Arabidopsis* (a model plant) and any crop plants. Examples of crop plants include, but are not limited to, rice, wheat, maize, potato, rape (Brassica), tomato, and soybean.

A method for disrupting a gene using a tobacco retrotransposon according to the present invention comprises the steps of: introducing the retrotransposon into the plant; and culturing a plant into which the retrotransposon has been introduced so that the plant is regenerated, thereby producing a plant with a disrupted gene.

A retrotransposon may be introduced into a plant body using any method known to those skilled in the art. Examples of well-known methods include methods mediated by *Agrobacterium* and a method of directly introducing a gene into a cell. An example of a method mediated by *Agrobacterium* is Nagel et al.'s method (Microbiol. Lett., 67, 325 (1990)). In this method, for sample, an expression vector is first introduced into *Agrobacterium* by electroporation, and the transformed *Agrobacterium* is then introduced into a plant cell in accordance with the method described in Plant Molecular Biology Manual (S. B. Gelvin et al., Academic Press Publishers). Examples of a known method for directly introducing a gene into a cell include electroporation methods and gene gun methods.

A cell into which a gene has been introduced may be selected for drug resistance, such as hygromycin resistance, and thereafter regenerated into a plant body using a commonly used method. As culture medium for regeneration into a plant body, any solid medium or liquid medium which are typically used in the art may be used. In the case of culture in solid medium, a callus, a shoot, or a root may be induced by adjusting the amount of plant hormones (auxin and cytokinin) in the medium for induction. In the case of suspension culture using liquid medium, a callus is regenerated into an adventive embryo and then a more complete plant body. In order to produce an adventive embryo, tissues such as the hypocotyl and leaf are initially cultured in auxin-containing medium. A yellow granular callus (EC) is grown and can be further subcloned. Thereafter, the callus is transferred to auxin-free medium in which an adventive embryo is produced. An example of the above-described induction medium includes typical solid or liquid Murashige-Skoog basal medium (Murashige T, Skoog F. 1962. Physiol. Plant. 15:473–497). With regard to these plant hormones, artificially-synthesized compounds having hormone activity are more preferable than naturally-occurring hormones. A preferable example of a medium used in regeneration into a plant body includes the regeneration medium described in Valvekens et al., PNAS, 85, 5536–5540 (1988). Culture may be conducted under predetermined conditions, e.g., at a temperature of 22° C. for about four weeks.

Thereafter, a regenerated plant body may be analyzed as to transposition of a retrotransposon. Examples of techniques used in such analysis include Southern hybridization for examining DNA and Northern hybridization for examining RNA. For analysis, for example, a technique utilizing a modified retrotransposon in which a marker gene having an intron in a direction reverse to transcription may be used. The analysis can also be conducted for a descendent plant obtained by propagating the regenerated plant. This is because Tto1 is stably passed onto the next generation in a Mendelian manner as described herein. Transposition of Tto1 occurs during the processes that take place between introduction of Tto1 and production of a plant having a disrupted gene (current generation).

Figure 2:
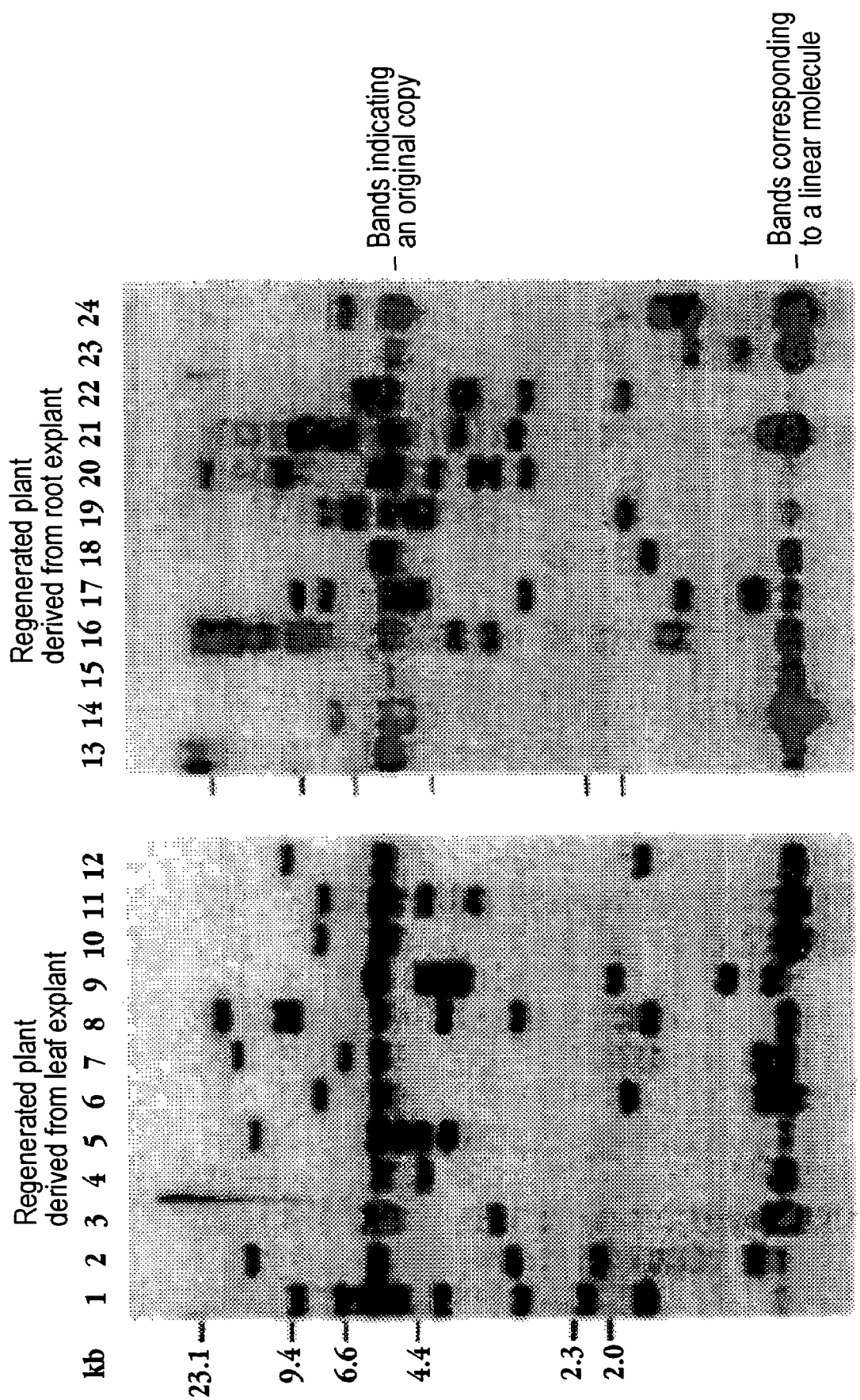
FIG. 2 is a photograph showing a DNA gel produced by Southern blot analysis of Tto1 transposition in *Arabidopsis*. 1.0 μg of genomic DNA isolated from a separate regenerated plant was digested with XbaI, followed by electrophoresis. The blot was probed with $^{32}$P-labeled 0.3 kb XbaI/PstI fragments of Tto1 (corresponding to 4284 to 4688). Bands corresponding to an original T-DNA copy and bands corresponding to linear molecules are shown. Lanes 1 to 12 indicate DNA isolated from plants regenerated from leaf explants, and Lanes 13 to 24 indicate DNA isolated from plants regenerated from root explants, respectively.

It has been known that transposition of Tto1 is activated by culture in tobacco (Hirochika, EMBO J. 12, 2521–2528 (1993)). Therefore, Tto1 was examined as to whether or not transposition is activated in *Arabidopsis* by culture. It had been speculated that transposition is highly active in transformed plants with high transposition copy numbers. Contrary to speculation, however, a high level of activation of transposition was observed only when a transformed plant having no or little transposition was used (FIG. 2).

A plant used in gene disruption according to the present invention may have a small copy number of retrotransposons. The term "small copy number" as used herein refers to 1 to 5 copies, preferably 1 to 3 copies, more preferably 1 to 2 copies, and most preferably 1 copy. A transformed plant having a small copy number is selected and thereafter, the plant is regenerated in tissue culture, thereby efficiently activating transposition leading to gene disruption. Screening may be conducted using the above-described analysis.

In order to analyze a disrupted gene, tissue from a regenerated plant may be probed against the transposed retrotransposon in order to recover sequences flanking the retrotransposon. The flanking sequences may be amplified by PCR. PCR amplification methods are well known in the art (PCR Technology: Principles and Applications for DNA Amplification, Edited by HA Erlich, Freeman Press, New York, N.Y. (1992); PCR Protocols: A Guide to Methods and Applications, Edited by Innis, Gelfland, Snisky, and White, Academic Press, San Diego, Calif. (1990); Mattila et al. (1991) Nucleic Acids Res. 19: 4967; Eckert, K. A. and Kunkel, T. A. (1991) PCR Methods and Applications 1: 17; PCR, McPherson, Quirkes, and Taylor, IRL Press, Oxford, these are herein incorporated by reference). The oligonucleotide primers used in the present invention are typically obtained by the method described herein. Alternatively, the oligonucleotide primer used in the present invention may be obtained by chemical synthesis based on the sequence disclosed herein. For example, the oligonucleotide primer used in the present invention may be synthesized using an oligonucleotide synthesizer (manufactured by Applied Bio Systems) in accordance with the specification provided by the manufacturer. Thereafter, the flanking sequences may be sequenced using well-known methods in the art. The determined sequence may be identified using any homology search program well known in the art.

Genes to be disrupted in accordance with the method of the present invention are exemplified, but not limited to, those described in Table 1 below.

In one embodiment of the present invention, the method of the present invention further comprises the steps of: obtaining a descendent plant from the above-described plant with a disrupted gene; and culturing tissue from the descendent plant to be regenerated into a plant body. As described above, since the retrotransposon Tto1 is inherited in a Mendelian manner, a plant of a subsequent generation to the subject plant, having a transposed retrotransposon may be used to perform gene disruption.

It was found that Tto1 can be utilized as a means for gene isolation by transposon tagging in *Arabidopsis*, which was not believed to have an active retrotransposon. A method of obtaining a separate gene disruption line by culture and regeneration using a retrotransposon has been known to be effective for an endogenous retrotransposon, such as Tos17 in rice. The present invention is the first demonstration that the method is applicable to a heterologous retrotransposon.

It was also found that, unlike DNA type transposons, retrotransposons can randomly transpose into chromosomes. Using this system, disruption lines covering all genes of *Arabidopsis* can be efficiently produced.

The gene disruption method of present invention is applicable to not only *Arabidopsis*, but also to any plant into which a gene can be introduced.

As described above, when a gene disruption method using a retrotransposon is established, the possibility of functional analysis of a gene in a plant and isolation of an unknown gene is increased.

EXAMPLES

Hereinafter, the present invention will be described by way of examples. The examples below are intended to illustrate the present invention. The present invention is not limited to the examples.

Example 1

Construction of the Binary Plasmid pBITto1 (−36) and Introduction into *Agrobacterium*

FIG. 1 shows a structure of pBTto1 (−36). A 5' portion of pSKTto1 (−36) (Hirochika et al., 1996, Plant Cell, 8, 725–734), which is a clone of Tto1 as previously reported, was excised with HindIII and PstI, and a 3' portion was excised with PstI and XhoI. The resultant Tto1 fragments were inserted into the binary vector pB1101-Hm digested with HindIII and SalI (Akama et al., Plant cell Rep. 12, 7–11 (1992)), thereby constructing the binary vector pBITto1 (−36) into which Tto1 was integrated. The thus-constructed plasmid was introduced into *Agrobacterium tumefaciens* strain EHA101 by electroporation (Hood et al., J. Bacteriol. 168, 1291–1301 (1986)). The strains into which Tto1 was introduced were screened in LB agar medium (10 g/l Bacto Tryptone (manufactured by Difco), 5 g/l Bacto Yeast Extract (manufactured by Difco), 10 g/l NaCl, 15 g/l Bacto Agar (manufactured by Difco), 50 µg/ml kanamycin sulfate (pH 7.0), and 50 µg/ml hygromycin B (pH 7.0) (Sigma)).

Example 2

Infection of Plants

*Arabidopsis* ecotype Wassilewskija (WS) was used in all experiments described below. A root or a hypocotyl of *Arabidopsis* was infected with *Agrobacterium* in accordance with the method of Akama et al. (1992) (Plant Cell Rep., 12, 7–11). The medium used in this example is described in Valvekens et al., PNAS, 85, 5536–5540 (1988). Briefly, pieces of hypocotyl and root of sterilely grown *Arabidopsis* plants, were cultured in CIM (callus inducing medium, containing 3.19/1 Gamborg's B5, 20 g/l glucose, 0.5 g/l MES-KOH (pH 5.7), 0.5 mg/l 2,4-D, and 0.05 mg/l kinetin, and 5 g/l Gellan Gum) at 22° C. for about 10 days (in the light for 16 hours and in the dark for 8 hours). Thereafter, the hypocotyl and root pieces were infected with *Agrobacterium*. The medium was replaced with new CIM. The hypocotyl and root pieces were co-cultured with *Agrobacterium* for three days.

After *Agrobacterium* was washed out, the above-described root or hypocotyl pieces were cultured in SIM (shoot induction medium containing 3.1 g/l Gamborg's B5, 20 g/l glucose, 0.5 g/l MES-KOH (pH 5.7), 0.15 mg/l IAA (indole-3-acetic acid), 5 mg/l 3-ipN$^6$-(2-isopentenyl)adenine, 5 g/l Gellan Gum and 50 ug/ml hygromycin), at 22° C. for four weeks (in the light for 16 hours and in the dark for 8 hours). The fragments were transferred to new medium every week, and were further cultured. As a result, a transformed plant (T0) was obtained. A regenerated shoot was transferred to GM (germination medium containing 4.4 g/l Murashige and Skoog Salt, 10 g/l sucrose, and 0.5 g/l MES-KOH (pH5.7), and 5 g/l Gellan Gum), and cultured. Thereafter, the shoot was transferred to RIM (root induction medium containing 4.4 g/l Murashige and Skoog Salt, 10 g/l sucrose, 0.5 g/l MES-KOH (pH 5.7), and 20 μg/l IBA(indole-3-butyric acid, and 5 g/l Gellan Gum), and cultured.

Example 3

Confirmation of Transposition by Southern Hybridization

DNA was prepared from the plant with a disrupted gene, obtained in Example 2 by cetyltrimethyl ammoniumbromide (CTAB) precipitation (Murray and Thompson, Nucleic Acids Res. 8, 4321–4325 (1980)). The isolated DNA was digested with the restriction enzyme EcoRV, followed by agarose gel electrophoresis. The DNA was transferred to a nylon membrane. DNA fragments derived from the Tto1 region, which had been prepared from plasmid pSKTto1 (−36), were labeled with $^{32}$P-dCTP, followed by Southern hybridization as described in Hirochika, EMBO J., 12, 2521–2528 (1993). The fragments were examined for the copy number of T-DNA by Southern hybridization using a hygromycin-resistance gene labeled with $^{32}$P-dCTP (Multiprime DNA labeling system, Amersham Pharmacia Biotech) (Hirochika, EMBO J., 12, 2521–2528 (1993)).

The copy number of Tto1 was expected to be greater than the copy number of introduced genes after transposition had occurred. The result of the analysis shows that plants ranging from no transposition to 15 transposed copies were obtained.

A subsequent generation (T1) of plants with disrupted genes was similarly analyzed. As a result, it was revealed that the Tto1 sequence was inherited to a subsequent generation in a Mendelian manner, and new transposition did not occur. This indicates that the Tto1 transposition observed in the plants having disrupted genes (T0) occurs during the process of production of said plants.

Example 4

Activation of Transposition by Culture

It has been reported that in tobacco Tto1 transposition is activated by culture (Hirochika, EMBO J. 12, 2521–2528 (1993)). Therefore, in this example, activation of Tto1 transposition by culture was examined.

Using the method described in Example 2 except for the step of *Agrobacterium* infection, leaf and root pieces of a plant having a disrupted gene (T2), which had been sterilely grown, were cultured, thereby obtaining 298 regenerated plant bodies (R0). The resultant plants were potted. At the same time, the plants were also pooled for DNA extraction. Seeds were obtained from 255 regenerated plant bodies; the remaining plant bodies were sterile. DNA was prepared from shoots of the R0 plants in a manner similar to that of Example 3. Thereafter, Southern Blot hybridization was conducted to examine the transpositional activity of Tto1 (an increase in copy number).

FIG. 2 shows the results of such an experiment using the leaf and root of a seedling which was of T2 generation subsequent to a plant (T1) into which one copy of Tto1 had been introduced. It had been speculated that a high level of activation of transposition would occur in plants having large transposition copy numbers (not shown). Contrary to the speculation, a high level of activation of transposition was observed only when plants having no transposition were used (FIG. 2).

Example 5

Analysis of Gene Disruption

DNA was prepared from the regenerated plant identified in Example 4, in which Tto1 transposition was activated by culture and the copy number increased, in the CTAB method described in Example 3. This DNA was used as a template to amplify sequences flanking Tto1 by TAIL-PCR. Reaction conditions and thermal cycling settings were as described by Liu et al (Liu et al., Plant J. 8, 457–463 (1995)). Briefly, LA-Taq (Takara Shuzo) was used for Taq polymerase. The sequences of Tto1-specific primers were as follows:

SEQ ID NO: 1 (Tto1-R1) 5'-TGGATATGAATAGTGC-CCGTATGG-3' (outside nested primer (corresponding to 652 to 629 of Tto1));

SEQ ID NO:2 (Tto1-R2) 5'-TACTCTAACCAAAGCTCT-GATACC-3' (inside nested primer (corresponding to 601 to 578 of Tto1)).

In addition, three different arbitrary primers were used. The sequences were as follows:

SEQ ID NO: 3 (AD1) 5'-NGTCGA(G/C)(A/T)GANA(A/T)GAA-3';

SEQ ID NO: 4 (AD2) 5'-GTNCGA(G/C)(A/T)CANA(A/T)GTT-3';

SEQ ID NO: 5 (AD3) 5'-(A/T)GTGNAG(A/T)AN-CANAGA-3'.5

Secondary TAIL-PCR products were separated by electrophoresis using a 1.2% low-melting-point agarose gel (SeaPlaque GTG, FMC, Rockland, Me.). A PCR product was purified from a thin strip excised from an agarose gel using Qiaquick Gel Extraction Kit (Qiagen, Valencia, Calif.). The purified product was subjected to direct sequencing with ABI 377 DNA sequencer (Perkin Elmer/Applied Biosystems) using Big Dye Terminator Cycle Sequencing Ready Reaction kit (Perkin Elmer/Applied Biosystems, Foster City, USA). The sequencing primer used was the following:

SEQ ID NO: 6 (Tto1-R1) 5'-CTCACTAAGGAGAGTTG-CATC-3' (corresponding to 69 to 49 of Tto1)).

A homology search was conducted for flanking sequences of Tto1 using BLAST (Altrschal et al., Nucleic. Acids Res. 25, 3389–3402 (1997)). The results are partially shown in Table 1 below.

TABLE 1

Homology search and mapping of transposition sites of Tto1

| | | | | | | |
|---|---|---|---|---|---|---|
| 1 | 3 | Partial CDS, (*Arabidopsis*, 3377807, AF075597), Zinc finger protein? | 63 | 9.00E−10 | P1, MUL8, ch.5, AB00954 | ch. V/ 79.0 cM |
| 2 | 6 | Proline-rich protein APG isolog, (*Arabidopsis*, 2062167, AC001645) | 78 | 2.00E−14 | P1, MED24, ch.5, AB005235 | V/7.1 |
| 3 | 8 | Hypothetical protein (*Campylobacter*) | 29 | 5.2 | | |
| 4 | 10 | | | | P1, AB009054, Ch.5 | |
| 5 | 12 | Glucosyltransferase (*Arabidopsis*, Z97335), 100% | 258 | 1.00E−68 | ESSA I contigfragment No.0, ch.4, Z97335 | |
| 6 | 16 | ATP dependent dsDNA exonuclease, (Aquifex, 2984155) | 31 | 1.3 | | |
| 7 | 20 | Hypothetical protein (*Arabidopsis*, 3805763, AC005693), 100% | 136 | 2.00E−32 | BAC, T25N22, ch.2, AC005693 | II/18.6 |
| 8 | 21 | | | | Nested Tto1 | |
| 9 | 22 | Hypothetical protein (*Arabidopsis*, e1250518, AL021811) 100% | 177 | 2.00E−44 | BAC, F10M6, ch.4, AL021811 | |
| 10 | 24 | Expansin (*Arabidopsis*, At-EXPS, 1041704, U30478) | 40 | 0.007 | | |
| 11 | 26 | tRNA-glutamine synthetase, (*Lupinus luteus*, e1284527, X91787) | 76 | 1.00E−13 | | |
| 12 | 28 | Similar to hin1 (harpin-induced gene 1) (*Arabidopsis*, 3193310, AF069300) | 85 | 2.00E−16 | P1, MHF15, ch.5, AB006700 | V/17.9 |
| 13 | 35 | | | | P1, MUB3, Ch.5, AB010076 | V/123.2 |
| 14 | 36 | F8M12.2 (*Arabidopsis*, 3513734), F8M12.4, F8M12.5 gene product | 72 | 5.00E−13 | BAC, F8M12, AF080118 | |
| 15 | 38 | NAM-like protein, 100% (*Arabidopsis*, 3695377, AF096370) 3695374, 3695378 | 87 | 5.00E−17 | BAC, F1I04, AF096370 | IV/8.7 |
| 16 | 39 | Receptor-like kinase, 100%? (*Arabidopsis*, 3236253, AC004684) | 105 | 8.00E−23 | BAC, F13M22, Ch.2, AC004684 | II/68.9 |
| 17 | 41 | *C. elegans* ESTyk317e7.5 (e1247655, Z99282) | 32 | 1.6 | | |
| 18 | 42 | Serine/threonine kinase (Sorghum bicolor, e1184909, Y12464) | 45 | 1.00E−04 | | |
| 19 | 43 | *C. elegans* hypothetical protein (e257868, 278064) | 34 | 0.12 | BAC, F23E12, ch.4, AL022604 | IV/84.8 |
| 20 | 44 | | | | Nested Tto1 | |
| 21 | 47 | | | | BAC, T128, ch.2, U78721 | II/64.3 |
| 22 | 57 | Hypothetical protein (*Arabidopsis*, 3337367, AC004481) | 49 | 2.00E−10 | | |
| 23 | 66 | Putative protein (Mybs?) (*Arabidopsis*, e1248723, AL021637) | 77 | 2.00E−15 | | |
| 24 | 72 | | | | into LTR of Tto1? | |
| 25 | 77 | Olfactory receptor ODR-10, (*C. elegans*, 2921626, U42830) | 29 | 3.9 | BAC, T8F5, ch.1, AC004512 | I/90.3 |
| 26 | 79 | | | | P1, MNJ8, ch.5, AB017069 | |
| 27 | 80 | Hypothetical protein similar to T18A10.3, (*Arabidopsis*, 2262177, AC002329) | 46 | 6.00E−05 | | |
| 28 | 82 | EST T21788 (*Arabidopsis*, 2341027, AC000104), 100% | 164 | 2.00E−40 | BAC, F19P9, ch.1, AC000104 | |
| 29 | 85 | CLV1 receptor kinase (*Arabidopsis*, 2160756, U96879) | 38 | 0.044 | | |
| 30 | 86 | Reverse gyrase (Aquifex, 2983417, AE000712) | 30 | 2.1 | | |
| 31 | 92 | | | | P1, MQJ16, ch.5, AB012244 | V/42.3 |
| 32 | 95 | | | | BAC, F18A17, ch.5, AC005405 | V/57.0 |
| 33 | 97 | CdsF (*Borrelia burgdorferi*, 1655793, U43414) | 30 | 6.2 | BAC, T4E14, ch.2, AC005171 | II/18.6 |
| 34 | 105 | | | | BAC, T21L14, Ch.2, AC003033 | II/62.5 |
| 35 | 109 | Hypothetical protein, (*Arbidopsis*, 2194134, AC002062), 100%, co-repressor SIN3A | 102 | 1.00E−21 | BAC, F20P5, ch.1, AC002062 | I/107.4 |
| 36 | 110 | Similar to urnidylyl transferase, (*Arabidopsis*, 2829923, AC002291) | 61 | 1.00E−10 | BAC, F22K20, ch.1, AC002291 | I/114.2 |
| 37 | 115 | hairy protein (bHLH), (*Drosophila virilis*, P29303) | 31 | 4.1 | | |

TABLE 1-continued

Homology search and mapping of transposition sites of Tto1

| | | | | | | |
|---|---|---|---|---|---|---|
| 38 | 116 | | | | P1, MNJ8, ch.5, AB017069 | |
| 39 | 125 | Pristinamycin I syththetase 3,4 (*Streptomyces*, e30893) | 29 | 8.5 | | |
| 40 | 128 | | | | BAC, T26D22, repetitive seq.? | |
| 41 | 134 | Annexin p35 (*Lycopersicon*, 3378204, AF079231) | 42 | 0.001 | | |
| 42 | 140 | AtRAB8 (*Arabidopsis*, 2289961, 1182434) | 29 | 9.3 | | |
| 43 | 145 | Phosphoinositide-specific phospholipase C (*Arabidopsis*, D50804, S71170) | 100 | 8.00E−21 | PLC-C cDNA (D50804) | |
| 44 | 150 | | | | into LTR of Tto1? | |
| 45 | 165 | Urease (*Canavalia ensiformis*, 167228, M65260) | 56 | 2.00E−07 | | |
| 46 | 166 | MAP Kinase (*Arabidopsis*, 2191146, AF007269), NTF4, ATMPK4, ATMPK6, . . . | 106 | 6.00E−23 | MAPK cDNAs | |
| 47 | 170 | Germin-like protein (*Arabidopsis*, 1755162, U75192) | 43 | 7.00E−04 | germin cDNA | |
| 48 | 174 | EST (e1347911, Z77665, D64926) | 29 | 7.8 | | |
| 49 | 175 | | | | putative transmembrane protein AF049236 | |
| 50 | 176 | Hypothetical protein (*Arabidopsis*, 2252828, AF013293) | 42 | 1.00E−06 | | |
| 51 | 177 | Serine/threonine kinase (*Arabidopsis*, 3335352, AC004512) | 42 | 0.002 | | |
| 52 | 180 | | | | BAC, T14N5, ch.1, AC004260 | I/114.2 |
| 53 | 182 | HSVSB (Simian herpes B virus) glycoprotein D precursor (P36342) | 33 | 0.54 | | |
| 54 | 183 | | | | BAC, T20D16, ch.2, AC002391 | II/39.9 |
| 55 | 188 | Ste20-like kinase homolog (*Arabidopsis*, 3176674, AC03671) | 35 | 0.14 | | |
| 56 | 190 | Resistance gene (*Arabidopsis*, e327519, Z97342) | 58 | 3.00E−08 | P1, MXI10, ch.5, AB005248 | V/78.9 |
| 57 | 192 | Tenascin-eastern newt (A43902) | 31 | 6.9 | TAC, K21C13, ch.5, AB010693 | V/91.8 |
| 58 | 195 | alpa-N-acetylgalactosaminidase (*Mus musculus*, e1311488, AJ223966) | 29 | 8.3 | | |
| 59 | 200 | Phosphatidic acid phosphatase 3a (*Cavia porcellus*, 3641334, AF088283) | 71 | 5.00E−12 | | |
| 60 | 201 | Hypothetical protein (*Arabidopsis*, 326887, Z97336) | 65 | 3.00E−10 | BAC, F9H3, ch.4, 18.8cM, AF071527 | IV/18.8 |
| 61 | 205 | Malate oxidoreductase (*Oryza sativa*, P43279) | 59 | 4.00E−10 | BAC, F18A17, ch.5, 60.5cM, AC005405 | V/57.0 |
| 62 | 211 | Dihydrofolate reductase-thymidylate synthetase (*Daucus carota*, e1289612, AJ003139) | 37 | 3.00E−06 | repetitive seq. | |
| 63 | 212 | Similar to glycosyl hydrolases, (*Arabidopsis*, 3047123, AF058919) 100% | 92 | 1.00E−18 | BAC, F6N23, AF058919 | IV/4.5 |
| 64 | 214 | Similar to cytochrome P450, (*C. elegans*, e1347959, Z50742) | 29 | 8 | | |
| 65 | 217 | Chitinase (*Emericella nidulans*, d1025495, D87895) | 31 | 5.2 | | |
| 66 | 218 | | | | P1, MUB3, ch.5, AB010076 | V/123.2 |
| 67 | 221 | Protein phosphatase I catalytic subunit, (*Arabidopsis*, d1025195, AB000094), 100% | 63 | 1.00E−D9 | genomic, AB000094 | |
| 68 | 222 | Kinesin-like protein A (*Arabidopsis*, Q07970) | 79 | 3.00E−26 | repetitive seq. | |
| 69 | 226 | Auxin-responsive GH3-like protein, (*Arabidopsis*, 3650037, AC005396), 100% | 247 | 3.00E−65 | BAC, T26120, ch.2, AC005396 | II/29.2 |
| 70 | 228 | Urease (*Filobasidiella*, 3688063, AF006062) | 29 | 5.7 | | |
| 71 | 230 | FIN21.11 (*Arabidopsis*, 2760326, AC002130), glyoxal oxidase | 78 | 2.00E−17 | | |
| 72 | 231 | Thioredoxin M-type (pea, P48384) | 125 | 1.00E−28 | repetitive seq. | |
| 73 | 236 | | | | YAC, YUP8H12R, ch.1 AC002986 | 1/4.0 |

TABLE 1-continued

Homology search and mapping of transposition sites of Tto1

| | | | | | | |
|---|---|---|---|---|---|---|
| 74 | 242 | | | | into Tto1? | |
| 75 | 243 | Hypothetical protein (*Arabidopsis*, e327517, Z97342) | 47.3 | 1.00E−05 | | |
| 76 | 249 | | | | into Tto1? | |
| 77 | 251 | Hypothetical protein (*Arabidopsis*, e1249684, AL021713) | 123 | 1.00E−28 | BAC, T9A21, ch.4, AL031713 | IV/58.1 |
| 78 | 256 | Hypothetical protein, (*Arabidopsis*, 2392765, AC002534), myosin heavy chain | 94 | 1.00E−19 | | |
| 79 | 266 | | | | BAC, F1715, ch.4, AL031032 | IV/80.5 |
| 80 | 268 | Putative protein (*Arabidopsis*, e1287886, AL022605) | 71 | 2.00E−12 | P1, MQN23, ch.5, AB013395 | V/123.2 |
| 81 | 270 | Hypothetical protein (*Arabidopsis*, e1283955, AL022223) | 56 | 1.00E−07 | P1, M3E9, ch.4, AL022223 | |
| 82 | 277 | Putative protein (*Arabidopsis*, e1249669, AL021712) | 83 | 8.00E−22 | | |
| 83 | 278 | DNA-dependent RNA polymerase (*Methanobacterium*, 2622150, AE000876) | 36 | 0.2 | AE000876 | II/39.9 |
| 84 | 281 | Putative receptor kinase, (*Arabidopsis*, 2642433, AC002391), 100% | 90 | 3.00E−18 | BAC, T20D16, ch.2, AC002391 | II/68.9 |
| 85 | 286 | Putative serine/threonine kinase (*Arabidopsis*, 3786010, AC005499), 100% CDC2B, . . . | 173 | 5.00E−43 | BAC, T6A23, AC005499, ch. 2 | |
| 86 | 288 | Hypothetical protein (*Arabidopsis*, 2347195, AC002338) | 78 | 2.00E−14 | | |
| 87 | 289 | Hypothetical Protein (*Arabidopsis*, 3785969, AC005560), salt-inducible protein | 149 | 9.00E−36 | BAC, F219, ch.2, AC005560 | II/1.7 |
| 88 | 293 | Similar to Myb isolog T01024-1 (*Arabidopsis*, 3249080, AC004473) | 34 | 0.002 | | |
| 89 | 297 | Hypothetical protein, (*Arabidopsis*, 2347195, AC002338) | 53 | 3.00E−07 | | |
| 90 | 302 | ATHB-4 (HD-Zip) (*Arabidopsis*, P92953), 100% | 79 | 1.00E−14 | ATHB-4 (Y09582), BAC, T13E5, ch.2 (AC002388) | |
| 91 | 306 | DNA topoisomerase II, (*Arabidopsis*, P30182), 100% | 124 | 1.00E−28 | Topo II, (L21015) 100% | |
| 92 | 310 | | | | Nested Tto1 | |
| 93 | 311 | Similar to *S. pombe* hypothetical protein C3H1.10 (*C. elegans*, e1347126, Z66513) | 30 | 1.8 | P1, MRH10, ch.5., AB006703 | V/91.8 |
| 94 | 312 | putative receptor kinase, (*Arabidopsis*, 2462756, AC002292), 100% | 153 | 4.00E−37 | BAC, F8A5, AC002292, | I/84.3 |
| 95 | 315 | | | | Nested Tto1 | |
| 96 | 326 | | | | BAC, T6B13, ch.2, AC005398 | II/29.2 |
| 97 | 327 | Na/H antiporter (*Synechocystis* sp., d1017724, D90902) | 33 | 0.9 | | |
| 98 | 332 | Similar to ubiquitin conjugating enzyme (*C. elegans*, 1086704, U41026) | 31 | 2.2 | | |
| 99 | 336 | Putative zinc finger protein (*Arabidopsis*, 3341678, AC003672), Ring finger RHA3b, . . . | 48 | 9.00E−06 | | |
| 100 | 340 | Transcription Factor SF3 isolog (*Arabidopsis*, 2088643, AF002109), ~100% | 53 | 3.00E−07 | BAC, T28M21, ch.2, AF002109 | II/72.4 |
| 101 | 347 | Purple acid phosphatase, (*Arabidopsis*, e353232, Z99708) | 75 | 3.00E−13 | | |
| 102 | 348 | Su(s) Suppressor of sable, (*Drosophila virilis*, 671708, U20660) | 30 | 7.3 | | |
| 103 | 349 | Predicted protein, (*Arabidopsis*, e1248844, AL021B54), Branched-chain a.a. aminotransferase | 73 | 1.00E−12 | | |
| 104 | 350 | Hypothetical protein (*Plasmodium*, 3845215, AE001402) | 35 | 0.12 | ch.4, ESSA I contig fragment No. 1 Z97336 | |
| 105 | 355 | Putatitive apolipoprotein N-acyltransferase (*Treponema*, 3322520, AE001206) | 28 | 7.2 | | |
| 106 | 361 | Calmodulin-like protein, (*Arabidopsis*, P30188) | 72 | 1.00E−12 | BAC, P13H10, ch.2, AC005662 | II/78.5 |

TABLE 1-continued

Homology search and mapping of transposition sites of Tto1

| 107 | 363 | Putative receptor protein kinase (*Arabidopsis*, 3461838, AC005315) | 46 | 3.00E−05 | | |
|---|---|---|---|---|---|---|
| 108 | 368 | Hypothetical protein, (*Arabidopsis*, 3510258, AC005310) | 57 | 2.00E−08 | | |
| 109 | 371 | Putative protein (*Arabidopsis*, e1249569, AL021712) | 64 | 2.00E−10 | BAC, T10114, ch.4, AL021712? | IV 62.9 |
| 110 | 375 | Monooxygenase, (*Arabidopsis*, e1315911, AJ007587) | 67 | 5.00E−11 | ESSA I contig fragment 4, Z97339 | |
| 111 | 376 | Putative cytochrome P450, (*Arabidopsis*, 3927833, AC005727), 100%, DWARFS (Maize) | 173 | 3.00E−43 | BAC, F8N16, ch.2, AC005727 | II/56.2 |
| 112 | 377 | Putative cytochrome P450, (*Arabidopsis*, 2880052, AC002340) | 135 | 1.00E−31 | | |
| 113 | 379 | Hypothetical protein, (*Arabidopsis*, 3236239, AC004684), 100% | 54 | 4.00E−07 | | |
| 114 | 380 | Putative annexin, (*Arabidopsis*, 3785996, AC005499) | 57 | 6.00E−08 | BAC, T6A23, ch.2, AC005499 | II/68.9 |
| 115 | 381 | | | | P1, MAC9, ch.5, AB010069 | V/115.0 |
| 116 | 391 | frohB, frohA, (*Arabidopsis*, Y09581) | 53 | 9.00E−07 | | |
| 117 | 392 | Hypothetical protein, (*Arabidopsis*, 3337359, AC004481), 100%, Myb? | 144 | 1.00E−34 | BAC, F13P17, ch.2, AC004481 | II/66.8 |
| 118 | 394 | Senescence-associated protein 6, (*Hemerocallis*, 3551956, AF082031) | 34 | 0.46 | | |
| 119 | 396 | Unknown protein, (*Arabidopsis*, 3540193, AC004122), ~100% | 83.5 | 2.00E−16 | BAC, T2711, ch.1, AC004122 | I/9.3 |

The data shown in Table 1 confirmed that Tto1 was inserted into various genes.

Example 6

Mapping of Tto1 Transposition Target Sites

Figure 3:
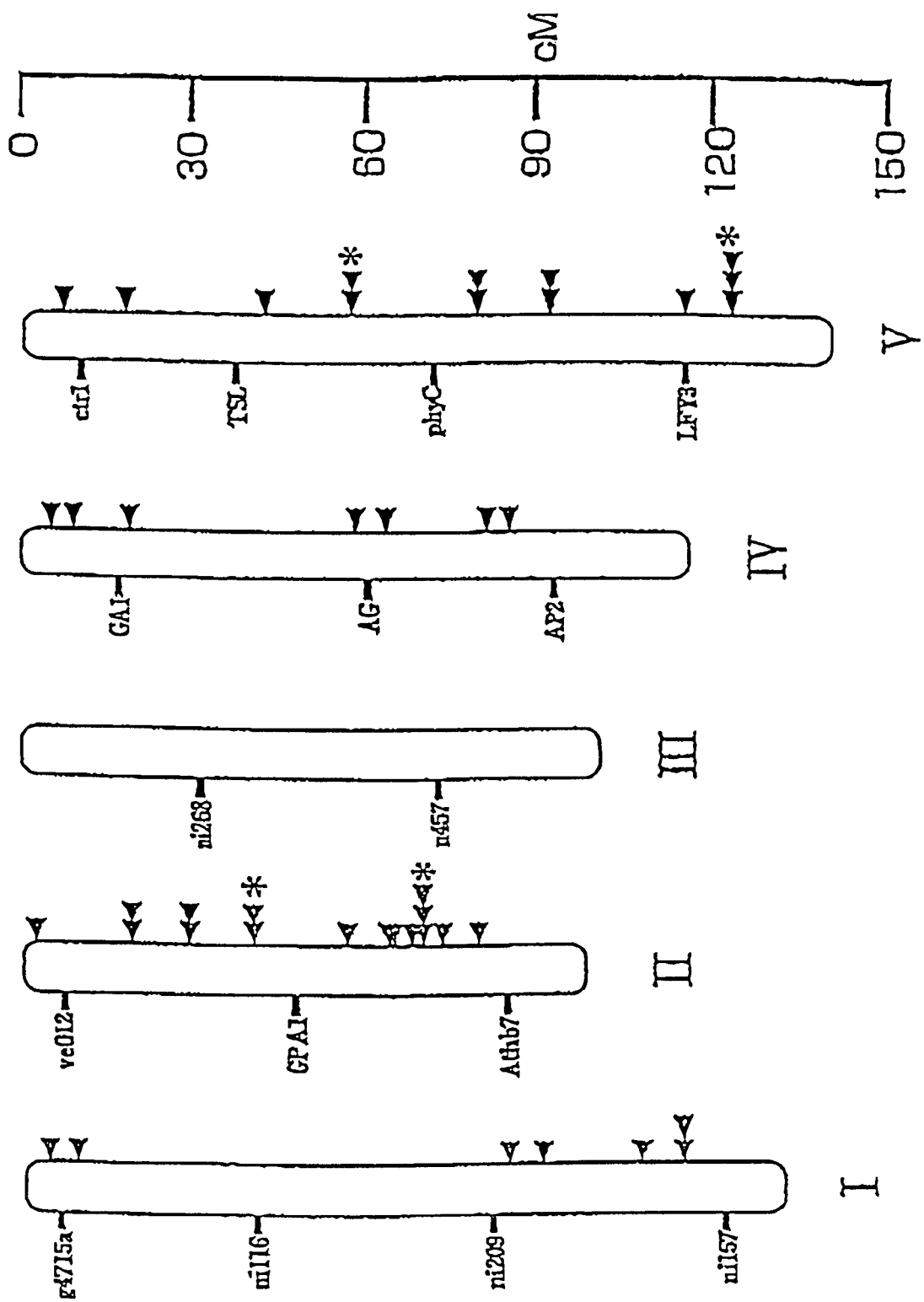
FIG. 3 is a diagram showing mapping of the transposition target sites of Tto1. The mapped genetic loci having Tto1 insertions are arranged with an RI map (Lister and Dean, Plant J. 4, 745–750 1993) and indicated by arrows. Each arrow indicates a separate insertion event. The scale of chromosome length is provided to the right. Several chromosome markers are shown in the map.

Homology analysis using BLAST revealed that Tto1 was inserted into various sequences which had to date been analyzed. Some of the sequences were mapped onto a chromosome. It is possible to map the point target sites of Tto1 based on such information (FIG. 3). As shown in FIG. 3, the tobacco retrotransposon Tto1 is different from maize transposons of in that Tto1 can transpose randomly in chromosomes. There were no cases when Tto1 was mapped onto the third chromosome, which is attributed to the fact that the database has very little information on base sequences of the third chromosome. The mark * indicates sites at which a plurality of transpositions were identified in a base sequence of the same BAC clone.

In the above-described examples, various aspects of the present invention, and how the specific oligonucleotide of the present invention was prepared, are illustrated and described. The present invention is not limited to these.

INDUSTRIAL APPLICABILITY

Novel means for gene disruption and gene isolation by transposon tagging is provided for *Arabidopsis*, in which it is believed that an active retrotransposon is not resent. A method of obtaining a separate gene disruption line by culture and regeneration using a retrotransposon was found to be applicable to heterologous retrotransposons. The gene disruption method of the present invention can be applicable to not only *Arabidopsis*, but also to any plant into which a gene can be introduced.

The retrotransposon Tto1 used in the present invention is different from DNA-type transposons, and can transpose randomly in chromosomes. Using this system, disruption lines covering all genes of *Arabidopsis* (a model plant) can be efficiently produced.

The invention claimed is:

1. A method for disrupting a gene in *Arabidopsis* plant comprising the steps of:
   introducing the tobacco Tto1 retrotransposon into *Arabidopsis* cell or tissue; and
   culturing and regenerating the *Arabidopsis* cell or tissue, into which the retrotransposon is introduced, to produce a plant having a disrupted gene; wherein the plant into which the Tto1 has been introduced has from 0 to 3 copy number of the Tto1 retrotransposons.

2. The method according to claim 1, wherein the copy number is 1 to 3 copies.

* * * * *